United States Patent
Walker et al.

(10) Patent No.: US 9,890,358 B2
(45) Date of Patent: Feb. 13, 2018

(54) LATENT NEURAL STEM CELL POPULATION

(75) Inventors: Tara Louise Walker, Fortitude Valley (AU); Perry Francis Bartlett, St. Lucia (AU)

(73) Assignee: The University of Queensland, St. Lucia (AU)

(*) Notice: Subject to any disclaimer, the term of this patent is extended or adjusted under 35 U.S.C. 154(b) by 226 days.

(21) Appl. No.: 12/595,220

(22) PCT Filed: Apr. 10, 2008

(86) PCT No.: PCT/AU2008/000511
§ 371 (c)(1),
(2), (4) Date: Feb. 4, 2010

(87) PCT Pub. No.: WO2008/124872
PCT Pub. Date: Oct. 23, 2008

(65) Prior Publication Data
US 2012/0195860 A1 Aug. 2, 2012

(30) Foreign Application Priority Data

Apr. 11, 2007 (AU) ................ 2007901902

(51) Int. Cl.

| | | |
|---|---|---|
| *A61N 2/00* | (2006.01) | |
| *A61K 35/30* | (2015.01) | |
| *C12Q 1/02* | (2006.01) | |
| *A61P 25/28* | (2006.01) | |
| *G01N 21/64* | (2006.01) | |
| *A61K 33/14* | (2006.01) | |
| *C12N 13/00* | (2006.01) | |
| *C12N 5/0797* | (2010.01) | |
| *A61N 1/36* | (2006.01) | |
| *A61K 33/00* | (2006.01) | |
| *A61K 35/12* | (2015.01) | |
| *A61N 1/20* | (2006.01) | |
| *A61N 1/32* | (2006.01) | |

(52) U.S. Cl.
CPC .......... *C12N 5/0623* (2013.01); *A61K 33/00* (2013.01); *A61K 33/14* (2013.01); *A61K 35/12* (2013.01); *A61N 1/205* (2013.01); *A61N 1/326* (2013.01); *A61N 1/36014* (2013.01); *C12N 2500/05* (2013.01)

(58) Field of Classification Search
None
See application file for complete search history.

(56) References Cited

FOREIGN PATENT DOCUMENTS

WO   WO 2004018655 A2 *  3/2004  ........... C12N 5/0623

OTHER PUBLICATIONS

Park, Youn-Kwan; et al; "Adenosine-mediated synaptic depression and EPSP/spike dissociation following high potassium-induced depolarization in rat hippocampal slices" Brain Research, 975, 237-243, 2003.*
Avis, Harry S; Carlton, Peter L; "Retrograde Amnesia Produced by Hippocampal Spreading Depression" Science, 73-75, Jul. 1968.*
Madsen, Torsten M; et al; "Increased Neurogenesis in a Model of Electroconvulsive Therapy" Biological Psychiatry, 47, 1043-1049, 2000.*
Morita, K; Katayama, Y; "Substance P Inhibits Activation of Calcium-Dependent Potassium Conductances in Gunea-Pig Myenteric Neurones" Journal of Physiology, 447, 293-308, 1992.*
Hsieh, Jenny; Gage, Fred H; "Epigenetic control of neural stem cell fate" Current Opinions in Genetics & Development, 14, 461-469, 2004.*
Rietze, Rodney L; et al; "Purification of a pluripotent neural stem cell from the adult mouse brain" Nature, 412, 736-739, 2001.*
Altman et al., "Autoradiographic and Histological Evidence of Postnatal Hippocampal Neurogenesis in Rats," J. Comp. Neur. 124(3): 319-336, Jun. 1965.
Batista et al., "A Progressive and Cell Non-Autonomous Increase in Striatal Neural Stem Cells in the Huntington's Disease R6/2 Mouse," J. Neurosci. 26(41): 10452-10460, Oct. 11, 2006.
Bengzon et al., "Apoptosis and proliferation of dentate gyrus neurons after single and intermittent limbic seizures," Proc. Natl. Acad. Sci. USA 94(19): 10432-14037, Sep. 16, 1997.
Brown et al., "Enriched environment and physical activity stimulate hippocampal but not olfactory bulb neurogenesis," Eur. J. Neurosci. 17(10): 2042-2046, May 2003.
Bull et al., "The Adult Mouse Hippocampal Progenitor Is Neurogenic But Not a Stem Cell," J. Neurosci. 25(47): 10815-10821, Nov. 23, 2005.
D'Ascenzo et al., "Role of L-type Ca2+ channels in neural stem/progenitor cell differentiation," Eur. J. Neurosci. 23(4): 935-944, Feb. 2006.
Deisseroth et al., "Excitation-Neurogenesis Coupling in Adult Neural Stem/Progenitor Cells," Neuron 42(4): 535-552, May 27, 2004.
Dolmetsch et al., "Signaling to the Nucleus by an L-type Calcium Channel-Calmodulin Complex Through the MAP Kinase Pathway," Science 294(5541): 333-339, Oct. 12, 2001.
Gage et al., "Survival and differentiation of adult neuronal progenitor cells transplanted to the adult brain," Proc. Natl. Acad. Sci. USA 92(25):11879-11883, Dec. 5, 1995.
Gil et al., "Reduced hippocampal neurogenesis in R6/2 transgenic Huntington's disease mice," Neurobiology of Disease 20(3): 744-751, 2005.
Goldman et al., "Neuronal production, migration, and differentiation in a vocal control nucleus of the adult female canary brain," Proc. Natl. Acad. Sci. USA 80(8): 2390-2394, Apr. 1983.
Gould et al., "Learning enhances adult neurogenesis in the hippocampal formation," Nat. Neurosci. 2(3): 260-265, Mar. 1999.
Jin et al., "Increased hippocampal neurogenesis in Alzheimer's disease," Proc. Natl. Acad. Sci. USA 101(1): 343-347, Jan. 6, 2004.
Kuhn et al., "Neurogenesis in the Dentate Gyrus of the Adult Rat: Age-Related Decrease of Neuronal Progenitor Proliferation," J. Neurosci. 16(6): 2027-2033, Mar. 15, 1996.

(Continued)

*Primary Examiner* — David W Berke-Schlessel
(74) *Attorney, Agent, or Firm* — Seed IP Law Group LLP (57) ABSTRACT

The present invention relates to a latent neural stem cell population which is capable of activation by membrane depolarization of a neural cell population, isolation and culture of same, and uses thereof.

8 Claims, 9 Drawing Sheets

(56) References Cited

OTHER PUBLICATIONS

Lois et al., "Proliferating subventricular zone cells in the adult mammalian forebrain can differentiate into neurons and glia," Proc. Natl. Acad. Sci USA 90(5): 2074-2077, Mar. 1, 1993.
Luskin, "Restricted Proliferation and Migration of Postnatally Generated Neurons Derived from the Forebrain Subventrivular Zone," Neuron 11(1): 173-189, Jul. 1993.
Mangiarini et al., "Exon 1 of the HD Gene with an Expanded CAG Repeat Is Sufficient to Cause a Progressive Neurological Phenotype in Transgenic Mice," Cell 87(3): 493-506, Nov. 1, 1996.
McEwen, "Corticosteroids and Hippocampal Plasticity," Ann. NY Acad. Sci. 746: 134-142, Nov. 1994.
Nakatomi et al., "Regeneration of Hippocampal Pyramidal Neurons after Ischemic Brain Injury by Recruitment of Endogenous Neural Progenitors," Cell 110(4): 429-441, Aug. 23, 2002.
Palmer et al., "The Adult Rat Hippocampus Contains Primordial Neural Stem Cells," Mol. Cell. Neurosci. 8(6): 389-404, 1997.
Palmer et al., "FGF-2-Responsive Neuronal Progenitors Reside in Proliferative and Quiescent Regions of the Adult Rodent Brain," Mol. Cell. Neurosci. 6(5): 474-486, Oct. 1995.
Palmer et al., "Vascular Niche for Adult Hippocampal Neurogenesis," J. Comp. Neurol. 425(4): 479-494, Oct. 2, 2000.
Parent et al., "Dentate Granule Cell Neurogenesis Is Increased by Seizures and Contributes to Aberrant Network Reorganized in the Adult Rat Hippocampus," J. Neurosci. 17(10): 3727-3738, May 15, 1997.
Parent et al., "Seizure-induced neurogenesis: are more new neurons good for an adult brain?" Prog. Brain Res. 135: 121-131, 2002.
Ramirez-Amaya et al., "Integration of New Neurons into Functional Neural Networks," J. Neurosci. 26(47): 12237-12241, Nov. 22, 2006.
Santarelli et al., "Requirement of Hippocampal Neurogenesis for the Behavioral Effects of Antidepressants," Science 301(5634): 805-809, Aug. 8, 2003.
Seaberg et al., "Adult Rodent Neurogenic Regions: The Ventricular Subependyma Contains Neural Stem Cells, But the Dentate Gyrus Contains Restricted Progenitors," J. Neurosci. 22(5): 1784-1793, Mar. 1, 2002.
Shors et al., "Neurogenesis in the adult is involved in the formation of trace memories," Nature 410(6826): 372-376, Mar. 15, 2001.
Tropepe et al., "Transforming Growth Factor-α Null and Senescent Mice Show Decreased Neural Progenitor Cell Proliferation in the Forebrain Subependyma," J. Neurosci. 17(20): 7850-7859, Oct. 15, 1997.
Van Praag et al., "Running enhances neurogenesis, learning, and long-term potentiation in mice," Proc. Natl. Acad. Sci. USA 96(23): 13427-13431, Nov. 9, 1999.
Walker et al., "The Doublecortin-Expressing Population in the Developing and Adult Brain Contains Multipotential Precursors in Addition to Neuronal-Lineage Cells," J. Neurosci. 27(14): 3734-3742, Apr. 4, 2007.
Walker et al., "Latent Stem and Progenitor Cells in the Hippocampus Are Activated by Neural Excitation," J. Neurosci. 28(20): 5240-5247, May 14, 2008.
Wallace et al., "Latent Stem Cells in the Hippocampus are Activated by Prolonged Seizures," Epilepsia 48(S6): 245-246, 2007.
Yanamoto et al., "Induced Spreading Depression Activates Persistent Neurogenesis in the Subventricular Zone, Generating Cells With Markers for Divided and Early Committed Neurons in the Caudate Putamen and Cortex," Stroke 36: 1544-1550, 2005.
Arvidsson et al., "Stroke Induces Widespread Changes of Gene Expression for Glial Cell Line-Derived Neurotrophic Factor Family Receptors in the Adult Rat Brain," *Neuroscience* 106(1):27-41, 2001.
Cilio et al., "Long-term Effects of Status Epilepticus in the Immature Brain Are Specific for Age and Model," *Epilepsia* 44(4):518-528, 2003.
Ekdahl et al., "Caspase inhibitors increase short-term survival of progenitor-cell progeny in the adult rat dentate gyms following status epilepticus," *European Journal of Neuroscience* 14:937-945, 2001.
Gould et al., "Stress and Hippocampal Neurogenesis," *Biol Psychiatry* 46:1472-1479, 1999.
Lazic et al., "Decreased hippocampal cell proliferation in R6/I Huntington's mice," *NeuroReport* 15(5):811-813, 2004.
Seki et al., "Age-related production of new granule cells in the adult dentate gyrus," *NeuroReport* 6:2479-2482, 1995.

\* cited by examiner

LATENT NEURAL STEM CELL POPULATION

TECHNICAL FIELD

The present invention relates to a latent neural stem cell population which is capable of activation by membrane depolarization of a neural cell population, isolation and culture of same, and uses thereof.

BACKGROUND ART

Many neurological diseases such as dementia, including Alzheimer's disease, stroke, depression, Parkinson's disease and motor neuron disease are associated with a reduction in the number of neurons. The decline in number of neurons may be rapid, as in the case of stroke, or slower, as in the case of Alzheimer's disease.

After heart disease and cancer, stroke is the third leading cause of death in western industrialized countries and the major cause of severe, long-term disability in adults with 56% of people following a stroke suffering from a severe or profound disability. There are over 20 million stroke survivors worldwide. Over 40,000 stroke events occur in Australia each year—one every 12 minutes, one every 45 seconds in the USA. This ailment represents an economic burden estimated to be $45 billion a year in the US alone and is expected to rise significantly. A significant factor contributing to this trend is the increased susceptibility to stroke among the elderly.

Alzheimer's disease is the most common dementia occurring in the elderly, affecting about 10% of people above 65 years and 40% above 80 years. Alzheimer's is predicted to afflict up to 16 million people by the middle of this century unless a cure or prevention is found in the United States alone. 50-75% of dementia is estimated to be caused by Alzheimer's disease. The prevalence of Alzheimer's disease is slightly higher in women than in men, but almost twice as many women live with dementia because of their longer life expectancy.

Alzheimer's disease is a progressive neurodegenerative disease characterized by memory loss and general cognitive and behavioural decline. Alzheimer's disease is commonly associated with a non-cognitive symptomatology including depression. Histologically, Alzheimer's diseased is defined by the presence in post-mortem human brain specimens of amyloid neuritic plaques, the formation of neurofibrillary tangles and degeneration of the cholinergic neurons.

Parkinson's disease is associated with the destruction of neurons, but the damage is restricted to the dopamine-producing cells in the substantia nigra (part of the basal ganglia). The most common symptoms of Parkinson's disease are tremor, rigidity and difficulty initiating movement. In the US alone, some one million patients are affected and 50,000 new patients are added annually.

Motor Neuron Disease is the name given to a group of diseases in which nerve cells that control the muscles degenerate and die. It is rarely diagnosed in people less than 30 years of age. In Australia, there are around 400 new cases of motor neuron disease each year. There is no effective method of treatment and the disease is generally fatal within 1-5 years of diagnosis. More than one person dies of Motor Neuron Disease each day in Australia.

There are several regions in the brain where stem cells are known to exist, including the sub-ventricular zone and the olfactory bulb. It is thought that the stem cells in these areas are already working at maximum capacity to generate new neurons for general "self-maintenance". Additionally, neurogenesis occurs in the subgranular cell layer of the adult hippocampal dentate gyrus and has important consequences in learning and memory (Shors et al., 2001). A number of environmental and behavioural stimuli have been shown to enhance hippocampal neurogenesis and this is thought to be mediated through synaptic activity (van Praag et al. 1999; Brown et al., 2003; Santarelli et al., 2003; McEwen, 1994). Since large numbers of hippocampal cells are generated throughout the lifetime of an animal it is predicted that a stem cell is most likely responsible. Surprisingly, however, the precursors identified so far that generate these cells have limited self-renewal (Bull and Bartlett 2005; Seaberg and van der Kooy et al., 2002). Despite the limited capacity for self-renewal of the cells so far identified, it has been shown that excitation caused by applying depolarizing levels of extracellular potassium mimics the effects of stably increased activity, as would occur in an active neural network, and leads to an increase in neuron production from hippocampal adult neural progenitor cells (Deisseroth et al., 2004).

SUMMARY OF THE INVENTION

The present inventors have found that there is a latent population of neural stem cells in the hippocampus additional to the known populations such as those in the sub-ventricular zone and the olfactory bulb, and different in character. They have found that membrane depolarization of a neural cell population in which these cells reside results in activation of this otherwise latent stem cell population and ultimately in increased neurogenesis. It is thought that this new source of neurons could play a critical role in the replacement of damaged and lost neurons in neurological diseases where neuron loss is a feature.

Accordingly, in one aspect, the present invention provides a method of activating a latent neural stem cell population contained within a neural cell population, comprising:

(1) providing a neural cell population;
(2) introducing the neural cell population to a culture medium; and
(3) activating the latent stem cell population by inducing membrane depolarization of the neural cell population.

In a further aspect, the present invention provides a method of isolating a neural cell population in which a latent neural stem cell population is activated, comprising:

(1) providing a neural cell population;
(2) introducing the neural cell population to a culture medium;
(3) activating the latent stem cell population by inducing membrane depolarization of the neural cell population; and
(4) selecting cells which demonstrate the property of self-renewal and multipotency.

In an embodiment the neural cell population is derived from the adult hippocampus, the olfactory bulb, spinal cord, cortex or cerebellum, whereas a latent stem cell population which responds to depolarization is not present in the sub-ventricular zone (SVZ). Although the expression of the protein Doublecortin (DCX) is associated with commitment of cells to the neuronal lineage, the cells which respond to depolarization are $DCX^{-ve}$. These cells have additionally been shown to bind the lectin peanut agglutinin (PNA) and so are considered to be $PNA^{+ve}$.

In an embodiment membrane depolarization is induced by increasing the ionic strength through the introduction of a metal salt. Typically the membrane depolarization is induced by the introduction of a potassium salt such as potassium chloride but may be induced with other salts such as barium salts.

In an embodiment activation occurs as a result of electrical excitation. Suitable means of electrical stimulation include electroconvulsive therapy, transcranial magnetic stimulation, deep brain stimulation and vagal nerve stimulation.

Accordingly, in a further aspect the present invention provides an in vitro culture in which an otherwise latent neural stem cell population has been activated by membrane depolarization, characterised in that the cell population is derived from the hippocampus, olfactory bulb, cortex, cerebellum or spinal cord but not the sub-ventricular zone and comprises cells which are self-renewing and multipotent, and which are $DCX^{-ve}$ and $PNA^{+ve}$.

In a further aspect, the present invention provides a composition comprising an otherwise latent neural stem cell population which has been activated by membrane depolarization, characterised in that the cell population derived from the hippocampus, olfactory bulb, cortex, cerebellum or spinal cord but not the sub-ventricular zone, and comprises cells which are self-renewing and multipotent, and which are $DCX^{-ve}$ and $PNA^{+ve}$, and a medium capable of supporting the growth of the cells.

In an embodiment the culture medium is a neurosphere-forming culture.

In a still further aspect, the present invention provides a method of establishing a cell population enriched for neural stem cells, comprising:

(1) providing a neural cell population;

(2) introducing the neural cell population to a neurosphere-forming culture medium;

(3) activating a latent stem cell population by inducing membrane depolarization of the neural cell population; and (4) selecting cells which demonstrate the property of self-renewal and multipotency and are $DCX^{-ve}$ and $PNA^{+ve}$.

It has been observed that the cells most likely to demonstrate the properties of self-renewal and multipotency are derived from neurospheres which are large in diameter, particularly those neurospheres larger in diameter than 110 µm and more particularly those neurospheres larger in diameter than 250 µm. Accordingly, in an embodiment neurospheres which have been subjected to activation and grow larger in diameter than 110 µm and more preferably larger in diameter than 250 µm are selected and prima facie identified as yielding a cell population in accordance with the invention for subsequent verification.

The method of the invention may further comprise inducing differentiation and proliferation.

Accordingly, in a further aspect the invention provides a composition comprising a neural cell population in which a latent neural stem cell population has been activated by inducing membrane depolarization and/or a cell population generated from said neural cell population by induction of differentiation and proliferation, and a medium capable of supporting the growth of the cells.

The expanded and activated stem cell population, or the progeny thereof following differentiation and proliferation, is likely to be useful in the treatment of neurodegenerative diseases to reverse the decline in the number of neurons characteristic of those diseases.

Accordingly, in a still further aspect the present invention provides a method for treating a neurodegenerative disease comprising administering to an animal in need of such treatment a composition as described above.

In an embodiment, the progeny of the stem cell population is introduced to the animal by transplantation involving implantation of the cells into the animal.

In particular, the discovery of this latent stem cell population opens the possibility that the in vivo population can be stimulated to proliferate and differentiate.

Accordingly, in a still further aspect the present invention provides a method of treating a neurodegenerative disease comprising initiating membrane depolarization to activate in vivo an otherwise latent neural stem cell population.

In an embodiment a metal salt is introduced into an animal brain, most particularly by injection. The injection may be a single injection, which may be over an extended period of time, or involve repeated injections over an extended period of time. The metal salt may be injected into the hippocampus, olfactory bulb, cortex, cerebellum or spinal cord. If injection is to the hippocampus this is typically to the dentate gyrus.

Typically the metal salt is a potassium salt such as potassium chloride.

In an embodiment the treatment comprises electrical excitation, in particular, electrical excitation selected from the group consisting of electroconvulsive therapy, transcranial magnetic stimulation, deep brain stimulation or vagal nerve stimulation and, most particularly, deep brain stimulation. Typically a stimulatory electrode is positioned in the hippocampus, olfactory bulb, cortex, cerebellum or spinal cord. If the electrode is located in the hippocampus this is typically in the dentate gyrus.

The stem cell population of the present invention is also useful as a model for the screening of potential neurologically active therapeutic compounds.

Accordingly, in one aspect of the present invention there is provided a method of screening a potentially neurologically active therapeutic compound comprising the steps of:

(1) providing a neural cell population in which a latent neural stem cell population is present;

(2) contacting said neural cell population with at least one candidate pharmaceutical agent; and (3) determining if said candidate agent has an effect on proliferation, differentiation, survival, phenotype or function of said neural cell population.

In an embodiment it is determined if the candidate agent activates the latent stem cell population.

In an alternative embodiment the effect of the candidate agent on a population in which the latent stem cell population has been activated is determined.

DETAILED DESCRIPTION OF THE INVENTION

The present invention relates to a latent population of stem cells which have been activated by membrane depolarization. The stem cell population thus identified is self-renewing and multipotent, and is DCX$^{-ve}$ and PNA$^{+ve}$. A latent stem cell population able to be activated in this way is present in the cortex, the olfactory bulb, the cerebellum and in the spinal cord, but a latent stem cell population of this type is not present in the sub-ventricular zone.

Any method of depolarization may be employed to activate the latent stem cell population of the present invention. While not wishing to be bound by theory it is believed that depolarization induces opening of L-type voltage-gated calcium channels. The L-type calcium channel typically opens in mature neurons in response to the depolarization provided by excitatory synaptic inputs. Thus excitation may be achieved through electrical signalling, but also through altering ionic concentrations in the environment of this cell or by contacting the cell with chemical agents that are specific modulators of activity of the calcium channel and serve to activate the channel. Voltage-sensitive calcium channels play an important role in regulating hormone and neurotransmitter release, muscle contraction, and a large number of other cellular functions. A modulator of activity of the calcium channel interacts with it, such as by binding to it, to alter the amount or duration of the biological activity of the calcium channel. An agonist of the calcium channel is a molecule that activates the calcium channel and so triggers an influx of calcium to the cell. The entry of calcium into a cell such as a mature neuron activates a signalling pathway and thus specifies a cellular response to calcium. Agonists of the calcium channel and the effects induced are known in the art. For example, they are sensitive to dihydropyridine agonists and antagonists. Antagonists of calcium channels comprise three different chemical classes: the dihydropyridine antagonists such as nifedipine, amlodipine, nitrendipine, nisoldipine and nicardipine; phenylalkylamines such as verapamil and benzothiazepines such as diltiazem. Modulators of activity can be proteins, carbohydrates, antibodies or low molecular weight molecules.

In addition to chemical modulation, activation can be achieved by electrical stimulation. This may be achieved by direct electrical excitation, for example, through electroconvulsive therapy, transcranial magnetic stimulation, deep brain stimulation or vagal nerve stimulation, or by altering the ionic strength of the environment of the cell. In an embodiment the ionic strength of the environment of the cell is increased by between 2 and 10 times, preferably between 4 and 6 times, most preferably about 5 times. In an embodiment, activation is achieved through contacting the cell with a potassium salt in excess of physiological concentration, for example, 10 to 30 mM potassium chloride, preferably 15 to 20 mM potassium chloride, most preferably 15 mM potassium chloride. In an alternative embodiment activation can be achieved through contacting the cell with a barium salt such as barium chloride.

Isolation of the neural cell population in which a latent stem cell population is activated allows for methods for screening drug candidates for effectiveness in increasing neurogenesis. Screening assays may be performed directly using a culture. Candidate agents may be initially screened for the ability to modulate neurogenesis through its effect on an in vitro culture. For example, in a method which involves contacting the candidate drug and the culture of the present invention, the effect on differentiation and proliferation of the stem cell population may be observed, but equally the effect on survival, phenotype or function of these cells or their progeny could be observed. An in vivo drug screening or drug discovery process involving engrafting a non-human mammal with an enriched population of neural stem cells is described in U.S. Pat. No. 7,105,150, the contents of which were incorporated herein by reference. The engrafted non-human mammal is useful for drug screening and drug discovery using well known methodology. Methods for screening a candidate agent against a cell culture are described, for example, in U.S. Pat. No. 7,041,438 using methods well known in the art. Assessment of the activity of candidate agents generally involves combining a cell culture with a candidate compound, determining any resultant change, and then correlating the effect of the compound with the observed change.

In addition, differentiated cells arising from the culture of the present invention can be used for tissue reconstitution or regeneration in a human patient in need thereof. The cells are administered in a manner that permits them to graft to the intended tissue site and reconstitute or regenerate the functionally deficient areas. Thus, the in vivo transplantation process comprises implanting members of the stem cell population of the present invention into a mammal once this population has been treated with one or more growth factors to induce differentiation, for example, once they have been induced to differentiate into neurons and/or glia. In vitro proliferation and differentiation of neural stem cells is described, for example, in U.S. Pat. No. 7,115,418, the contents of which are incorporated herein by reference. The growth factors necessary to induce proliferation and/or differentiation are well known to the person skilled in the art and include, but are not limited to, NGF, BDNF, the neurotrophins, CNTF, amphiregulin, FGF-1, FGF-2, EGF, TGFα, TGFβ, PDGF, IGFs and the interleukins.

EXAMPLE 1

Activation of Latent Stem Cell Population

Primary Neurosphere Cultures

Adult (6-8 week old) male C57/B16 mice were killed by cervical dislocation, their brains immediately removed and the hippocampus, SVZ, olfactory bulb or cortex dissected. The tissue was enzymatically digested with 0.1% trypsin-EDTA (Gibco/Invitrogen, Eugene, Oreg.) for 7 minutes at 37° C., followed by a wash with 0.014% w/v trypsin inhibitor (type I-S from soybean; Sigma-Aldrich. Australia, Sydney, Australia) dissolved in Hepes-buffered minimum essential medium (HEM), which consisted of minimum essential medium (Gibco/Invitrogen) supplemented with 16 mM HEPES (Sigma-Aldrich Australia) and 100 units/ml penicillin/streptomycin (Gibco/Invitrogene). The tissue was centrifuged at 100 rcf for 7 minutes, following which the pellet was resuspended in 1 ml neurosphere growth medium, mechanically triturated until smooth, then filtered through a 40 μm cell sieve (Falcon/BD Biosciences Australia, North Ryde, Australia). The neurosphere growth medium consisted of mouse NeuroCult™ NSC Basal Medium plus mouse NeuroCult™ NSC Proliferation Supplements (StemCell Technologies, Vancouver, Canada) with 2% bovine serum albumin (Roche, Basel, Switzerland) and 2 μg/ml heparin (Sigma-Aldrich Australia). The following growth factors were also included: 20 ng/ml purified mouse receptor-grade EGF (BD Biosciences Australia) and 10 ng/ml recombinant bovine FGF-2 (Roche). After centrifugation at 100 rcf for 7 minutes, the cells were plated at a density of approximately one hippocampus, SVZ or cortex or four olfactory bulbs per 96-well plate (Falcon/BD Biosciences Australia) with 200 μl neurosphere medium per well.

The neurosphere growth medium already contained 4.18 mM KCl. Therefore for the depolarization experiments, additional KCl was added to give the final KCl concentration of 15 mM. This level of potassium is around four times that of the normal physiological concentration of potassium, ~4 mM. Nicardipine (Sigma-Aldrich), when used, was added to a final concentration of 10 μM. BaCl was used as an alternative to KCl in some experiments at a concentration of 1 mM and GABA at 100 μM. Primary hippocampal cells were incubated for 10 days, and SVZ, olfactory bulb or cortical cells for 7 days, in humidified 5% $CO_2$ to permit neurosphere formation. The primary neurospheres were then counted and collected for passaging or differentiation. Results of the neurosphere counts were expressed as mean ± standard error and statistical analysis was performed using a standard t-Test (two sample assuming equal variance).

Figure 1:
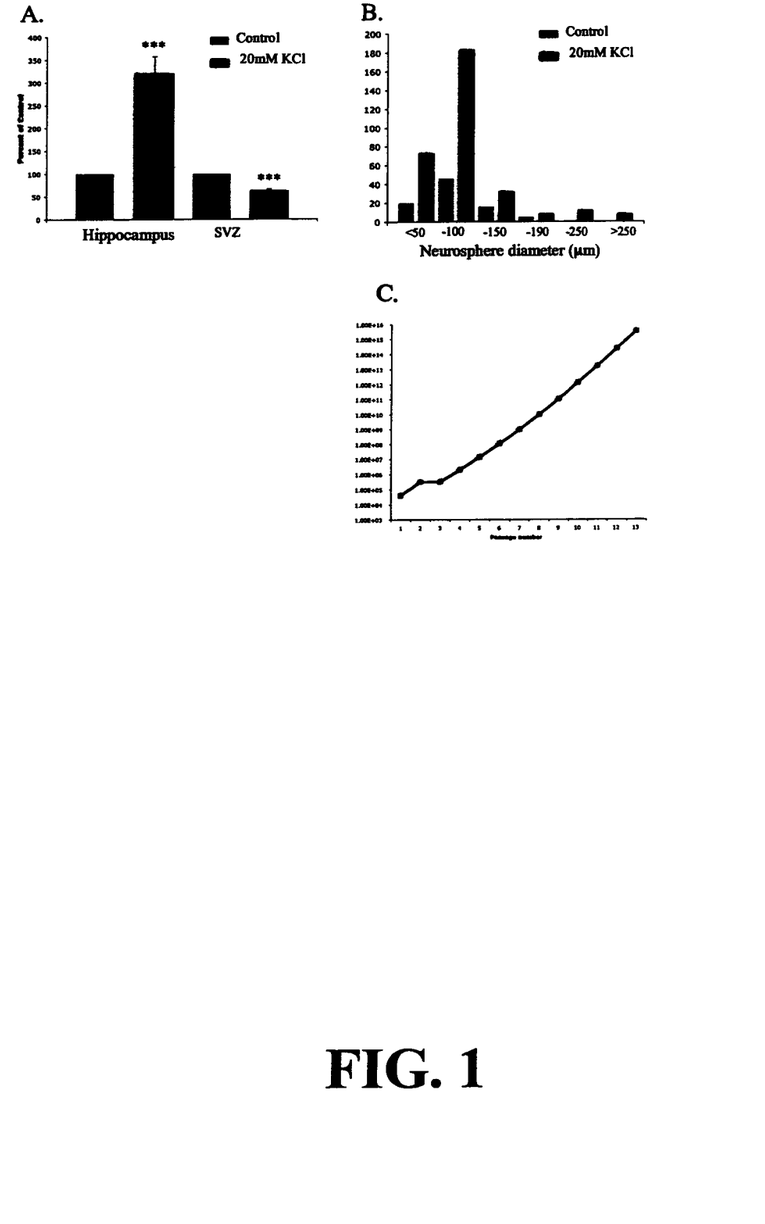
FIG. 1 shows potassium-induced activation of a latent neural stem cell population from the hippocampus and failure of a population from the sub-ventricular zone (SVZ) to activate it (A) graph showing degree of activation of cells in the hippocampus and SVZ in the presence and absence of potassium chloride (B) graph showing neurosphere diameter for hippocampal cells in the presence and absence of potassium chloride (C) graph demonstrating ability of potassium-activated cells to be passaged repeatedly.
Figure 2:
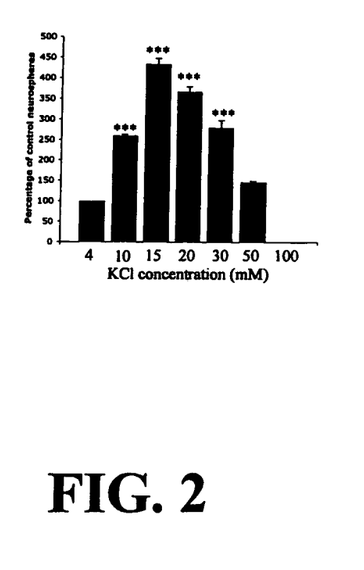
FIG. 2 is a graph showing the influence of potassium chloride concentration on cell activation.
Figure 3:
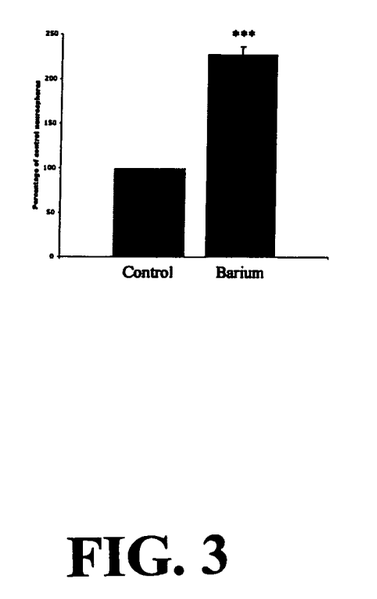
FIG. 3 is a graph demonstrating activation by barium chloride compared to a control of sodium chloride.

Dissociated, adult mouse hippocampal cells plated in neurosphere-forming media containing 15 mM KCl increased the number of neurospheres generated by over 3-fold compared to those cells plated in control (4 mM) potassium concentrations or non depolarizing control conditions in which an equivalent concentration of sodium was added as an osmotic control (FIG. 1a). A KCl a dose response assay further demonstrated that optimal depolarizing level was 15 mM KCl and that a concentration as low as 10 mM and as high as 30 mM will still significantly increase the number of neurospheres generated (FIG. 2). The ability to cause this activation is not restricted to depolarization using KCl as we show that $BaCl_2$ has similar effect with 1 mM $BaCl_2$ increasing the numbers of neurospheres over 2-fold (FIG. 3).

Figure 4:
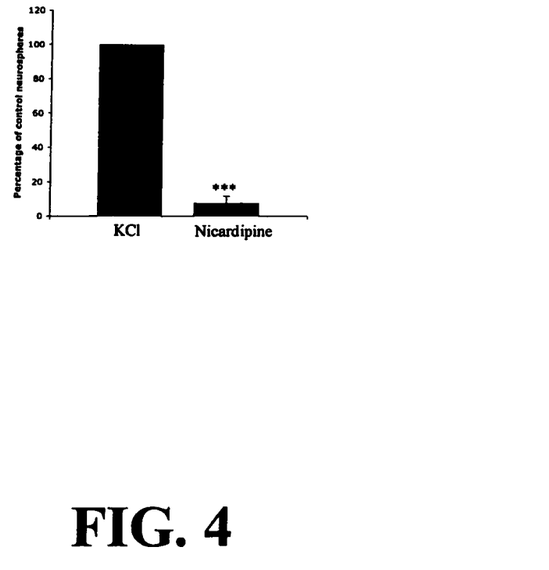
FIG. 4 is a graph showing inducement of activity with potassium chloride in the presence and absence of the L-type calcium channel antagonist, nicardipine.

The results show that potassium-induced depolarization stimulates the formation of increased numbers of large neurospheres in the hippocampus (FIGS. 1b and c). The results show further that the depolarization-induced activity of hippocampal precursors is also working through an L-type Ca2+ channel. The L-type Ca2+ antagonist nicardipine almost completely blocked this excitation-induced activation of neurosphere forming cells (FIG. 4).

Figure 6:
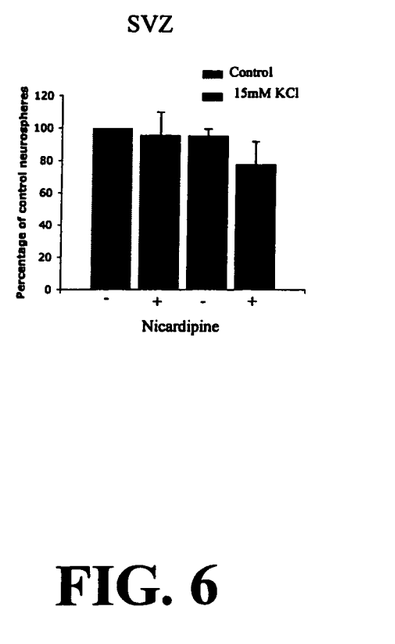
FIG. 6 demonstrates the inability to expand the cell population in the SVZ.
Figure 7:
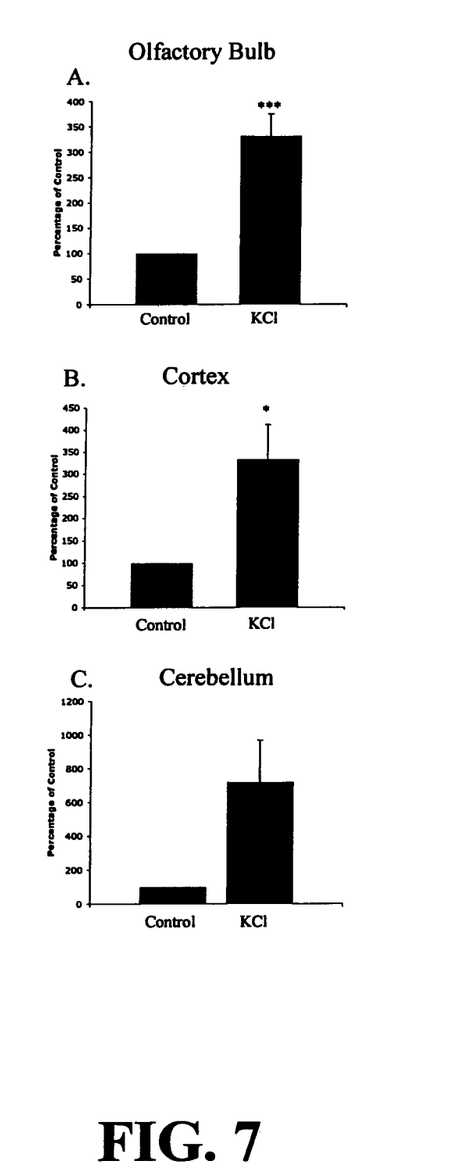
FIG. 7 demonstrates expansion of a cell population (A) in the olfactory bulb (B) in the cortex and (C) in the cerebellum.

However, potassium-induced depolarization does not increase the number of spheres in the adult SVZ. In fact it decreases neurosphere number by approx 40% (FIG. 6). While not wishing to be bound by theory, it is believed that this indicates that the stem cell population identified by the present invention is an entirely different population of stem cells to the one previously identified in the SVZ. Consistent with our results that potassium-induced depolarization does not activate the precursor cells resident in the SVZ, the behavioural paradigms affecting the hippocampus have been shown to have no impact on neurogenesis in the SVZ (Brown et al., 2003). In addition, the L-type Ca2+ channel antagonist nicardipine does not inhibit neurosphere formation in SVZ either in the presence or absence of depolarizing levels. of potassium. Neurogenesis in this region can however be increased by olfactory stimulation (Rochefort et al., 2002), further suggesting that different activity rules govern different local circuits. Consistent with this we show that like the hippocampal precursor, the precursor in the olfactory bulb can also be activated under depolarizing conditions. We observe an over 3-fold increase in the number of olfactory bulb neurospheres in the potassium-activated condition compared to control (FIG. 7). In addition there is a significant increase in the size of these activated olfactory-bulb neurospheres (FIG. 7). This population of latent cells may also be present in other non-proliferating areas. The cortex also showed an increase in neurosphere number in response to depolarization with over 3-fold more neurospheres generated (FIG. 7).

Neurosphere Differentiation

Neurospheres were plated onto poly-D-lysine coated coverslips in NeuroCult™ NSC Basal Medium containing mouse NeuroCult™ NSC Proliferation Supplements and 2% foetal calf serum without growth factors. The neurospheres were allowed to differentiate for 5 days in humidified 5% $CO_2$ until flattened and adherent. The differentiated neurospheres were then fixed with 4% paraformaldehyde (Sigma-Aldrich Australia, Sydney, Australia) in 0.1M PBS at room temperature for 30 minutes. After washing with PBS, they were stained for the neuronal marker βIII tubulin and the astrocytic marker glial fibrillary acidic protein (GFAP) with a DAPI counterstain (see below).

Immunocytochemistry

The cells were incubated for 60 minutes at room temperature with blocking solution: 5% foetal bovine serum (JHR Biosciences, Brooklyn, Australia) plus 5% normal goat serum (Sigma-Aldrich) in 0.1M PBS containing 0.1% triton X-100 (Sigma-Aldrich). The blocking solution was replaced with fresh solution containing mouse monoclonal βIII tubulin antibody (1:2000; Promega, Madison, Wis.) plus rabbit polyclonal GFAP antibody (1:500; DakoCytomation, Carpinteria, Calif.) and incubated for 60 minutes at room temperature. The cells were washed with PBS and incubated for 30 minutes at room temperature in blocking solution containing Alexafluor 568 anti-mouse antibody (1:1000; Molecular Probes/Invitrogen, Eugene, Oreg.), Alexafluor 488 anti-rabbit antibody (1:1000; Molecular Probes/Invitrogen) and DAPI (1:5000; Sigma-Aldrich). Following washing with PBS, the slides were coverslipped with fluorescent mounting medium (DakoCytomation) before viewing on a Zeiss upright fluorescent microscope. Images were captured by a digital camera linked to a computer running Axioscope version 4 (Zeiss, Göttingen, Germany).

Hippocampal Neurosphere Passaging

To determine whether the neurospheres generated under depolarizing conditions demonstrated the characteristic stem-cell properties of self-renewal and multipotentiality, primary neurospheres were individually dissociated and replated into media containing no additional potassium. Primary neurospheres from the unstimulated hippocampus were also passaged as single spheres.

Hippocampal neurosphere cultures were initiated by removing 150 µl of the medium from wells containing single neurospheres, treating with 100 µl 0.1% trypsin-EDTA for 2 minutes at room temperature, followed by washing with 100 µl trypsin inhibitor in HEM. The neurospheres were mechanically triturated until dissociated and replated in 24 well plates in 2 ml of complete medium. Neurospheres were passaged every 10 days by centrifuging the neurospheres, removing the medium and incubating in 1 ml of 0.1% trypsin-EDTA for 2 minutes at room temperature. After the addition of an equal volume of trypsin inhibitor, the neurospheres were centrifuged at 100 rcf for 5 minutes and the supernatant removed. Cells were mechanically triturated in 500 µl of complete medium and trypan blue staining was used to evaluate the number of cells, both viable and total number, on a hemocytometer. The passaged cells were then re-plated with complete medium at a density of $1 \times 10^4$ cells/cm$^2$ in tissue culture flasks (Nunc, Rochester, N.Y.) or tissue culture plates (Falcon/BD Biosciences) as appropriate.

A number of the potassium stimulated large primary spheres (23 out of 64) could be expanded in culture for up to 10 passages (FIG. 1c). All 23 of the KCl stimulated neurospheres capable of long term passage were large with a diameter of >110 µm. Subsequent passages of these hippocampal spheres showed high numbers of neurons when differentiated, indicating they are neurogenic. The primary potassium stimulated neurospheres however, contained mostly astrocytes similar to control neurospheres.

EXAMPLE 2

Latent Stem Cell Population is DCX$^{-ve}$

Generation of DCX-GFP/2 kb transgenic mice

A construct containing 2 kb of, the mouse DCX promoter, from −1802 bp to +199 bp relative to the translation start site in the plasmid pBluescript was obtained. A fragment containing the enhanced GFP gene (eGFP) and the SV40 poly A was removed from plasmid pEGFP1 (Clontech/BD Biosciences, Heidelberg, Germany) by digestion with SalI and AflII and blunt-ending the AflII site with Klenow. Unless otherwise noted, all enzymes were obtained from New England Biolabs (Frankfurt, Germany). The fragment containing the eGFP gene was cloned into SalI and BfrBI digested pBS-DCX to generate the clone pDCXeGFP. Plasmid DNA was purified using the plasmid maxiprep kit (Qiagen Australia, Melbourne, Australia), after which the DCXeGFP cassette was removed by digestion of 40 µg of DNA with SpeI, BsrBI and XmnI. Digested DNA was run on a 0.7% TBE gel and the insert purified using the Qiagen gel purification kit. Transgenic mice (DCX-GFP/2kb) were generated by pronuclear injection of the DNA cassette into fertilized BCBF1 mouse eggs, which were then implanted into pseudopregnant animals. DNA was isolated from the resulting offspring, and founder mice were identified via polymerase chain reaction (PCR) using primers DCXP2009F (5'-CAGAACCAGAACCTTGCAGGC-3') and eGFPR2 (5'-GCGCGGGTCTTGTAGTTGCCG-3'). The PCR conditions were 1 cycle of 94 C for 3 mins, followed by 40 cycles of 94 C for 30 sec, 60 C for 30 sec and 72 C for 30 sec, with a final cycle of 72 C for 7 mins.
Fluorescence Activated Cell Sorting E14, P2 and adult brains were collected as described above and processed either whole or dissected into specific regions (olfactory bulb, cortex, cerebellum and subventricular zone (SVZ)). GFP+ve cells were separated by fluorescence-activated cell sorting (FACS) using a FACS Vantage cell sorter (BD Biosciences). A wild-type littermate control was used to determine background fluorescence levels. For primary neurosphere cultures the cells were plated at a density of 500 cells/well in 96-well plates (Falcon/BD Biosciences, San Jose, Calif.) with 0.2 ml complete medium per well. Complete medium consisted of mouse NeuroCult™ NSC Basal Medium plus mouse NeuroCult™ NSC Proliferation Supplements (StemCell Technologies, Vancouver, Canada) with 2% bovine serum albumin (Roche, Basel, Switzerland) and 2 µg/ml heparin (Sigma-Aldrich). The following growth factors were also included: 20 ng/ml purified mouse receptor-grade epidermal growth factor (EGF; BD Biosciences Australia) and 10 ng/ml recombinant bovine basic fibroblast growth factor (FGF-2; Roche). Primary cells were incubated for 7 days in humidified 5% CO2 to permit neurosphere formation. The primary neurospheres were then counted and collected for passaging or differentiation. Results of the neurosphere counts were expressed as mean + or − standard error and statistical analysis was performed using a standard t-Test (two sample assuming equal variance).

Mice in which the green fluorescent protein (GFP) is driven by the Doublecortin (DCX) promoter (DCX-GFP) were used for the separation of DCX$^{+ve}$ cells. Hippocampus from adult DCX-GFP mice (see above) were dissected and processed as described. DCX-GFP$^{+ve}$ and DCX-GFP$^{-ve}$ cells were separated by fluorescence-activated cell sorting (FACS) using a FACS Vantage cell sorter (BD Biosciences) as described (see above). A wild-type littermate control was used to determine background fluorescence levels. Potassium was added to DCX$^{+ve}$ and DCX$^{-ve}$ cells at a final concentration of 15 mM and the number of neurospheres counted after 10 days.

Figure 5:
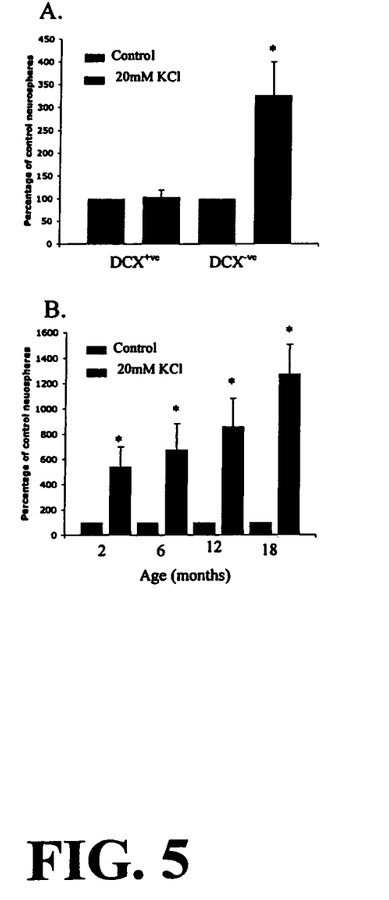
FIG. 5 demonstrates results for the potassium-activated cell population (A) a DCX$^{-ve}$ population is expanded by potassium induction (B)potassium-induced activation with increasing age of the hippocampus.

DCX is a 40aDa microtubule-associated protein that is expressed in migrating neuroblasts in embryos and is retained in neurogenic areas in the adult (the sub-ventricular zone/rostral-migratory stream/olfactory bulb access and the dentate gyrus of the hippocampus. The restriction of DCX expression to the neuronal precursor phase of the neuronal lineage has been verified (Brown et al, 2003). In the light of these recent demonstrations of DCX as a specific marker of neuronal progenitor cells which are committed to the neuronal lineage, it is noted that the DCX$^{+ve}$ hippocampal cells have a significantly higher neurosphere frequency than DCX$^{-ve}$ population. Although the DCX$^-$ population has a very low neurosphere-forming activity it is this population, and not the DCX$^{+ve}$ population, that responds to the high levels of potassium (FIG. 5a). Adult hippocampal cells were also separated based on their binding of the lectin peanut agglutinin. The PNA positive population is activated by potassium.

EXAMPLE 3

In Vivo Models

Brain insults such as ischemia and seizure, both of which cause acutely increased local excitation, have shown to cause activity-dependent proliferation in the DG (Arvidsson et al., 2001; Liu et al., 1998). Example 1 shows that there is a large latent population of stem cells which are activated by enhanced synaptic activity. To determine whether these cells can be activated in vivo two models, pilocarpine-induced epileptic seizures and Huntington's disease were investigated. Increased prolonged synaptic activity is seen during seizure therefore, we used this model to see if seizure could activate this latent population in vivo. Status epilepticus (SE) is defined as continuous seizures lasting for 30 mins or more and results in increased neurogenesis in the DG (Parent et al., 1997).

Pilocarpine-induced Seizures

Seizures were induced in 6-8 week old C57BL/6 male mice by the administration of pilocarpine, a muscarinic cholinergic agonist. Thirty minutes prior to pilocarpine administration, the mice were injected with 2.5 mg/kg of the cholinergic antagonist scopolamine methyl nitrate (Sigma-Aldrich) to reduce peripheral cholinergic effects. They then received intraperitoneal injections of 350 mg/kg pilocarpine hydrochloride (Sigma-Aldrich). Seizures were observed in 70% of the mice and of these 35% entered into status epilepticus 78±43 minutes after the injection of pilocarpine. Seizures were stopped 2 hours after status epilepticus onset, with an intraperitoneal injection of 5 mg/kg diazepam (Patulin, Parnell Laboratories Sydney, Australia). Mice that did not enter status epilepticus also received diazepam and were used as controls.

Figure 8:
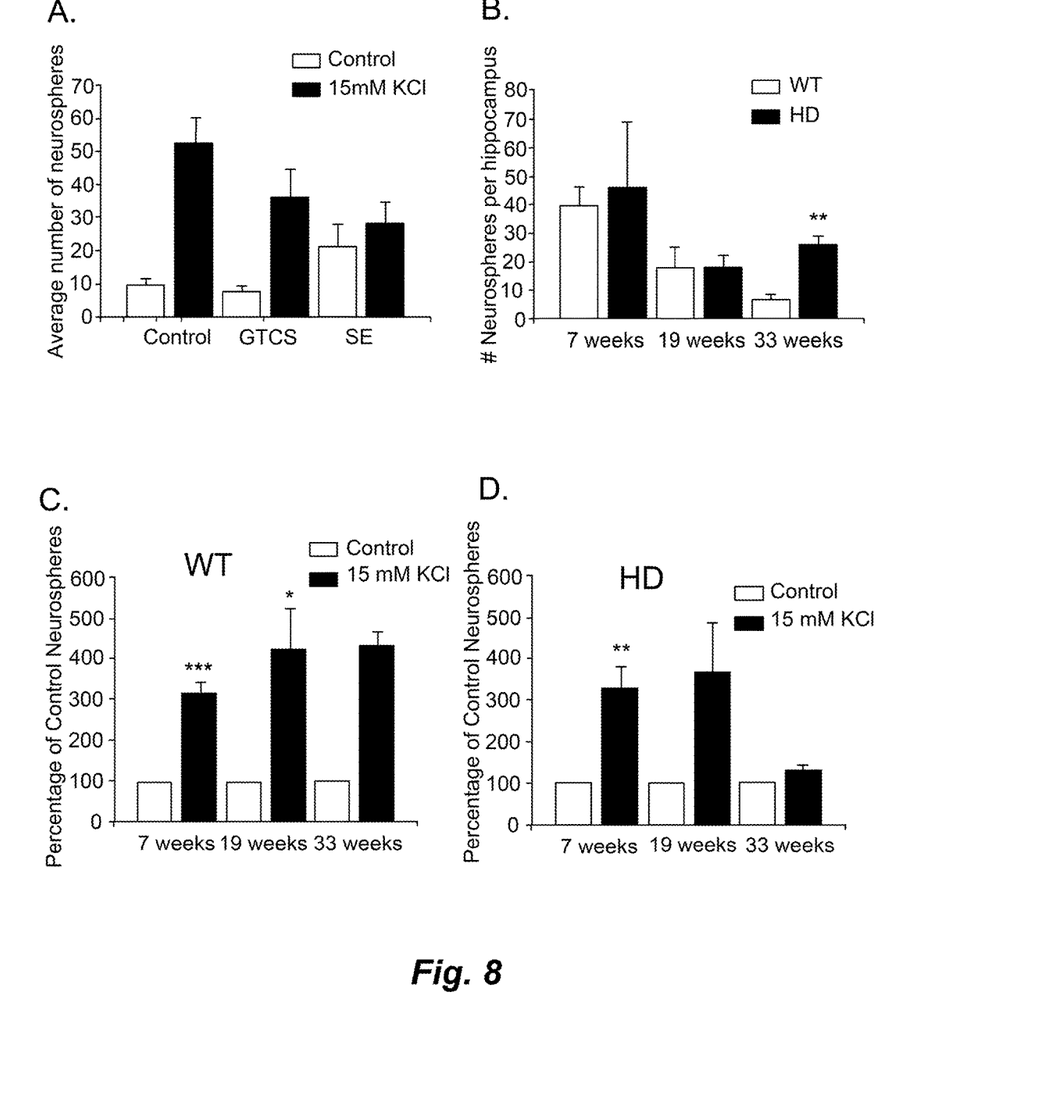
FIG. 8 shows results for in vivo models (A) demonstration of activation by induction of seizures in mice with injections of pilocarpine hydrochloride (B) demonstration of activation in Huntington's disease mice (C) activation with increasing age in wild type mice using potassium chloride and (D) equivalent experiment in Huntingdon's disease mice demonstrating that after 33 weeks potassium chloride could not further increase depolarization in vitro.
Figure 9:
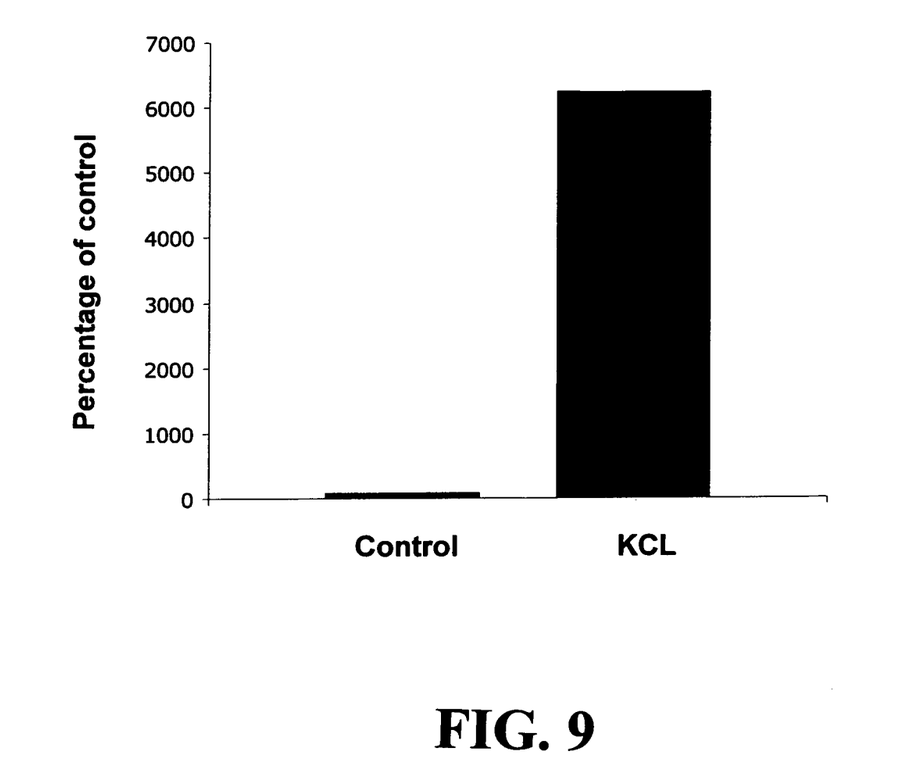
FIG. 9 is a plot of activation in cells derived from the spinal cord demonstrating activation with KCl.

Following SE there is considerable hippocampal damage (Cilio et al., 2003) and a transient increase in proliferation lasting 2-3 weeks (Parent et al., 1997) however, the majority of the new neurons do not survive beyond 4 weeks (Ekdahl et al., 2001). Interestingly, having a small number of seizures GTCS does not cause this significant increase in neurogenesis. Consistent with this increased synaptic activity, we show that mice which underwent SE for at least 2 hours and sacrificed after 48 hours showed a significant increase in the numbers of hippocampal neurospheres compared to control mice (FIG. 8). Interestingly, mice that suffered sporadic GTCS had no increase in hippocampal neurosphere numbers. Most importantly the latent precursors from mice that underwent SE were activated completely and addition of depolarizing levels of potassium had no further stimulatory effect indicating it is the same population of precursors (FIG. 8). In addition we observed that extended depolarization, between 24 and 48 hours exposure to high level of KCl is required for the stimulation to occur in WT hippocampus confirming the need for prolonged depolarization.

Injection of KCl

An injection of 40-50 mM KCl was made directly to the dentate gyrus over a period of 1-2 hours. As a control, injections are made be the other side of the hippocampus without KCl. delivery. The mice are left to recover for 2 days, and activation of the latent stem cell population is demonstrated using the neurosphere assay of Example 1.

Huntington's Disease Mice

R6/1 (B6CBA-TgN(HDexon1)61 Gpb/Pan) mice were originally obtained from Jackson Laboratory (Bar Harbor, Me.) and maintained by backcrossing to CBB6F1 females. For the neurosphere assays we used HD exon 1 carriers (R6/1) and aged matched wild-type littermates. Huntington's Disease is a neurodegenerative disorder that affects the striatum and cortex as well as hippocampus (Murphy et al., 2000). Previous studies have shown that older symptomatic R6/1 transgenic mice have a significant decrease in cell proliferation in the hippocampus compared to wild-type mice whereas younger pre-symptomatic R6/1 and WT mice had similar levels of proliferation (Lazic et al., 2004). In addition, neurogenesis failed to upregulate in the DG of R6/2 mice in response to seizures suggesting these mice have a lower capacity to mobilise neurogenesis in response to injury (Phillips et al., 2005). We observed a decrease in the total number of hippocampal neuroapheres with age in WT mice that was not observed in HD mice. Older symptomatic HD mice (33 weeks old) have significantly more neurospheres than the 33 week old WT mice, and a similar number of neurospheres to both the 19 week old WT and HD mice (FIG. 8). Consistent with the seizure model we found that the 33 week HD hippocampal precursors were activated completely and could not be further increased by potassium depolarization in vitro (FIG. 8).

An age related decrease has been shown to occur in the number of restricted progenitors but not in the number of neural stem cells in the subependyma (Tropepe etal, 1997), however an age related decrease of about 10-17% in cell proliferation below adult levels been shown (Kuhn et al., 1996; Seki and Ari, 1995). Conversely, no age-related attenuation of proliferation was observed in the lateral ventricle wall (Kuhn et al., 1996). We show that there is a significant decrease in the number of neurosphere-forming cells in the hippocampus as it ages (FIG. 5b). However, the percentage increase in cells stimulated by the depolarizing conditions increases with age. The greatest increase was observed in the oldest animals we tested with the 18 month old hippocampus demonstrating an over 12-fold increase in the number of neurospheres formed in the stimulated compared to control conditions. Consistent with mechanisms of regulation of neurogenesis, animals with low neurogenesis, for example the DBA mouse strain, have a smaller latent population and show a decreased percentage of activation.

EXAMPLE 4

Mice were anaesthetised with pentobarbital and supplemented throughout surgery as required. They were fixed in a stereotaxic frame. An midline incision was made, then the skin retracted and the skull scraped free of connective tissue. Burr holes for recording electrode and stimulating electrode and ground were made in the skull, the dura was removed. The recording electrode lowered into the hilus of the dentate gyrus (AP-2, ML 1.2-1.4). The stimulating electrode was lowered into the perforant path (AP lambda, ML 2.5). Depth of stimulating and recording electrodes was adjusted based on the evoked responses generated by low frequency stimulation. After placement of electrodes, a 15 min baseline was recorded under low-frequency stimulation followed by delivery of tetanus stimulation to induce LTP. After HFS, a 45 min post-baseline was recorded under low-frequency stimulation. After recording, electrodes were removed, the akin was sutured and mice were returned to their home cages. Stored data of fEPSP slope and population spike amplitude were used for determination of the presence or absence of LTP.

INDUSTRIAL APPLICABILITY

The ability to activate this latent stem cell population pharmacologically in vivo may have important clinical implications particularly if they are/can be activated to repopulate the damaged hippocampus after brain injuries such as stroke or ischemia leading to some degree of long-range connections and improved functional recovery.

REFERENCES

The contents of the following documents cited within the preceding description are incorporated herein by reference.

C. M. Batista, T. E. Kippin, S. Willaime-Morawek, M. K. Shimabukuro, W. Akamatsu, D. van der Kooy, *J. Neurosci.* 26, 13411 (2006).

J. Brown, C. M. Cooper-Kuhn, G. Kempermann, H. van Praag, J. Winkler, F. H. Gage, H. G. Kuhn, *Eur. J. Neurosci.* 17, 2042 (2003).

N. D. Bull, P. F. Bartlett, *J. Neurosci.* 25, 10815 (2005).

K. Deisseroth, S. Singla, H. Toda, M. Monje, T. D. Palmer, R. C. Malenka, *Neuron* 42, 535 (2004).

B. S. Mc Ewen, *Ann. N Y Acad. Sci.* 746, 134 (1994). S. A. Goldman, F. Nottebohm, *Proc. Natl. Acad. Sci. USA* 80, 2390 (1983).

L. Mangiarini, K. Sathasivam, M. Seller, B. Cozens, A. Harper, C. Hetherington, M. Lawton, Y. Trottier, H. Lehrach, S. W. Davies, G. P. Bates, *Cell* 87, 493 (1996).

J. M. Parent, T. W. Yu, R .T. Leibowitz, D. H. Geschwind, R. S. Sloviter, D. H. Lowenstein, *J. Neurosci.* 17, 3727 (1997).

V. Ramirez-Amaya, D. F. Marrone, F. H. Gage, P. F. Worley, C. A. Barnes, *J. Neurosci.* 26, 12237 (2006).

L. Santarelli, M. Saxe, C. Gross, A. Surget, F. Battaglia, S. Dulawa, N. Weisetaub, J. Lee, R. Durman, O. Arancio et al., *Science* 301, 805 (2003).

R. M. Seaberg, D. van der Kooy, *J. Neurosci.* 22, 1784 (2002).

T. J. Shors, G. Miesegaes, A. Beylin, M. Zhao, T. Rydel, E. Gould, *Nature* 410, 372 (2001).

H. van Praag, B. R. Christie, T. J. Sejnowski, F. H. Gage, *Proc. Natl. Acad. Sci. USA* 96, 13427 (1999).

C. Lois, A. Alvarez-Buylla, Proc. Natl. Acad. Sci. USA 90, 2074 (1993).

M. B. Luskin, Neuron 11, 173 (1993).

J. Altman, G. D. Das, J. Comp. Neurol. 124, 319 (1965).

H. G. Kuhn, H. Dickinson-Anson, F. H. Gage, J. Neurosci. 16, 2027 (1996).

T. D. Palmer, A. R. Willhoite, F. H. Gage, J. Comp. Neurol. 425, 479 (2000).

F. H. Gage, P. W. Coates, T. D. Palmer, H. G. Kuhn, L. J. Fisher, J. O. Suhonen, D. A. Peterson, S. T. Suhr, J. Ray, Proc. Natl. Acad. Sci. USA 92, 11879 (1995).

T. D. Palmer, J. Ray, F. H. Gage, Mol. Cell Neurosci. 6, 474 (1995).

T. D. Palmer, J. Takahashi, F. H. Gage, Mol. Cell Neurosci. 8, 389 (1997).

E. Gould, A. Beylin, P. Tanapat, A. Reeves, T. J. Shors, Nat. Neurosci. 2, 260 (1999).

H. Nakatomi, T. Kuriu, S. Okabe, S. Yamamoto, O. Hatano, N. Kawahara, A. Tamura, T. Kirino, M. Nakafuku, Cell 110, 429 (2002).

K. Jin, A. L. Peel, X. O. Mao, L. Xie, B. A. Cottrell, D. C. Henshall, D. A. Greenberg, Proc. Natl. Acad. Sci. USA 101, 343 (2004).

R. E. Dolmetsch, U. Pajvani, K. Fife, J. M. Spotts, M. E. Greenberg, Science 294, 333 (2001).

T. L. Walker, T. Yasuda, D. J. Adams, P. F. Bartlett, J. Neurosci. 27, 3734 (2007).

J. M. Gil, P. Mohapel, I. M. Araujo, N. Popovic, J. Li, P. Brundin, A. Petersen, Neurobiol. Disease 20, 744 (2005).

V. Tropepe, C. G. Craig, C. M. Morshead, van der Kooy, J. Neurosci. 17, 7850 (1997).

J. M. Parent, D. H. Lowenstein, Prog. Brain Res. 135, 121 (2002).

J. Bengzon, Z. Kokaia, E. Elmer, A. Nanobashvili, M. Kokaia, O. Lindvall, Proc. Natl. Acad. Sci. U.S.A. 94, 10432 (1997).

The invention claimed is:

1. A method of activating a latent neural stem cell population contained within a neural cell population to promote proliferation of the latent neural stem cells, comprising:
   (1) providing a neural cell population, wherein the neural cell population comprises one or a plurality of latent neural stem cells that are present as dissociated cells from adult hippocampus, wherein the latent neural stem cells are not proliferating; and
   (2) introducing the neural cell population to a neurosphere-forming culture medium under conditions which induce membrane depolarization of the neural cell population to promote proliferation of otherwise latent neural stem cells in the plurality of latent neural stem cells and formation therefrom of neurospheres,
   wherein the neural stem cells that proliferation are self-renewing, multipotent and are $DCX^{-ve}$ and $PNA^{+ve}$, and proliferation of the neural stem cells causes an increase in number of neurospheres that comprise the neural stem cells that are self-renewing, multipotent and are $DCX^{-ve}$ and $PNA^{+ve}$.

2. The method of claim 1 wherein membrane depolarization is induced by increasing ionic strength through introduction of a metal salt.

3. The method of claim 2 wherein membrane depolarization is induced by the introduction of a potassium salt.

4. The method of claim 2 wherein membrane depolarization is induced by the introduction of a barium salt.

5. The method of claim 2 wherein the salt is added to the culture medium.

6. The method of claim 1 wherein activating comprises electrical excitation.

7. An in vitro neurosphere culture in which an otherwise latent neural stem cell population has been activated by the method of claim 1, characterised in that the neurosphere culture comprises a cell population that (i) is derived from dissociated cells from adult hippocampus, and (ii) comprises cells which are self-renewing and multipotent, and which are DCX−ve and PNA+ve, wherein the self-renewing and multipotent cells are contained in neurospheres.

8. The in vitro culture of claim 7, wherein the neurospheres have a diameter of greater than 100 μm.

* * * * *

UNITED STATES PATENT AND TRADEMARK OFFICE
CERTIFICATE OF CORRECTION

PATENT NO. : 9,890,358 B2  
APPLICATION NO. : 12/595220  
DATED : February 13, 2018  
INVENTOR(S) : Tara Louise Walker et al.

Page 1 of 1

It is certified that error appears in the above-identified patent and that said Letters Patent is hereby corrected as shown below:

In the Claims

Column 14, Line 49:
"DCX-ve and PNA+ve, wherein the self-renewing and multipotent"
Should read:
--$DCX^{-ve}$ and $PNA^{+ve}$, wherein the self-renewing and multipotent--.

Signed and Sealed this
Sixth Day of November, 2018

Andrei Iancu
*Director of the United States Patent and Trademark Office*